(12) United States Patent
Cesa et al.

(10) Patent No.: US 7,211,674 B2
(45) Date of Patent: May 1, 2007

(54) PROCESS FOR THE RECOVERY OF OXAZOLE

(75) Inventors: Mark C. Cesa, Wheaton, IL (US); Eric J. Moore, Wheaton, IL (US); Mark R. Bruce, Seven Hills, OH (US); Sanjay P. Godbole, Solon, OH (US); Michael K. Hagans, Lima, OH (US); David R. Bender, Lima, OH (US)

(73) Assignee: Ineos USA LLC, Lisle, IL (US)

( * ) Notice: Subject to any disclaimer, the term of this patent is extended or adjusted under 35 U.S.C. 154(b) by 438 days.

(21) Appl. No.: 10/738,571

(22) Filed: Dec. 17, 2003

(65) Prior Publication Data

US 2004/0230059 A1 Nov. 18, 2004

Related U.S. Application Data

(60) Provisional application No. 60/442,359, filed on Jan. 24, 2003, provisional application No. 60/438,419, filed on Jan. 7, 2003.

(51) Int. Cl.
*C07D 263/02* (2006.01)

(52) U.S. Cl. .................................... 548/215
(58) Field of Classification Search ................ 548/215
See application file for complete search history.

(56) References Cited

U.S. PATENT DOCUMENTS

| 3,044,966 | A | | 7/1962 | Callahan et al. |
|---|---|---|---|---|
| 3,198,750 | A | | 8/1965 | Callahan et al. |
| 3,359,158 | A | | 12/1967 | Pence et al. |
| 3,522,268 | A | | 7/1970 | Hall et al. |
| 3,524,875 | A | | 8/1970 | Hadley et al. |
| 3,541,131 | A | | 11/1970 | Darcas et al. |
| 3,642,930 | A | | 2/1972 | Grasselli et al. |
| 3,686,263 | A | | 8/1972 | Maute et al. |
| 3,911,089 | A | | 10/1975 | Shiraishi et al. |
| 4,208,329 | A | * | 6/1980 | Smiley ..................... 548/239 |
| 4,237,303 | A | | 12/1980 | Gatling |
| 4,362,603 | A | | 12/1982 | Presson et al. |
| 4,474,709 | A | * | 10/1984 | Jordan ..................... 558/435 |
| 4,485,079 | A | | 11/1984 | Brazdil et al. |
| 4,503,001 | A | | 3/1985 | Grasselli et al. |
| 4,767,878 | A | | 8/1988 | Grasselli et al. |
| 4,863,891 | A | | 9/1989 | Grasselli et al. |
| 4,873,215 | A | | 10/1989 | Brazdil, Jr. et al. |
| 4,877,764 | A | | 10/1989 | Glaeser et al. |
| 5,093,299 | A | | 3/1992 | Suresh et al. |
| 6,780,289 | B2 | * | 8/2004 | Godbole ..................... 203/79 |

FOREIGN PATENT DOCUMENTS

GB 1130846 10/1968

* cited by examiner

*Primary Examiner*—Kamal A. Saeed
(74) *Attorney, Agent, or Firm*—David P. Yusko

(57) ABSTRACT

A process for the recovery of oxazole comprising contacting a mixture comprising oxazole and acetonitrile with an acid to form an acid salt of oxazole; separating acid salt of the oxazole from the mixture; and neutralizing the acid salt of oxazole separated from the mixture to release oxazole.

18 Claims, No Drawings

PROCESS FOR THE RECOVERY OF OXAZOLE

This application claims the benefit of U.S. Provisional Application No. 60/438,419 having a filing date of Jan. 7, 2003 and U.S. Provisional Application No. 60/442,359 having a filing date of Jan. 24, 2003.

BACKGROUND OF THE INVENTION

This invention relates to a process for the recovery of oxazole from mixtures comprising oxazole. This invention relates to the recovery of oxazole from mixtures comprising oxazole and one or more of acetonitrile, acrylonitrile and, optionally, water. This invention relates to the recovery of oxazole from process streams produced during the manufacture of acrylonitrile, and more particularly by the manufacture of acrylonitrile by the catalytic ammoxidation of propylene or propane. This invention also relates to the purification of oxazole.

Oxazole is a heterocyclic organic compound having the molecular formula $C_3H_3NO$. It is a liquid at ambient temperatures. The 52nd edition of the CRC Handbook of Chemistry and Physics reports the boiling point of oxazole as 69–70° C. Oxazole is used as a starting material for the preparation of a variety of other organic compounds. It is useful as an insecticide; see for example U.S. Pat. No. 3,359,158. It is also useful as a solvent.

Oxazole is not readily synthesized. It is, however, produced as a minor impurity during the manufacture of acrylonitrile by the catalytic ammoxidation of a hydrocarbon feed, such as propylene or propane, in the presence of ammonia and an oxygen-containing gas.

The art needs a process to isolate such oxazole in an effective and efficient manner that provides oxazole in useful quantities and of a sufficient purity so that it can be used for the above-mentioned applications as well as other uses. The present invention provides such an effective and efficient process.

SUMMARY OF THE INVENTION

This invention is a process for the recovery of oxazole comprising contacting a mixture comprising oxazole and one or more other organic components, for example, acetonitrile, with an acid to form an acid salt of oxazole, separating the acid salt of the oxazole from the mixture, and neutralizing the acid salt of oxazole separated from the mixture to release oxazole.

This invention is a process for the recovery of oxazole from a mixture comprising oxazole and one or more other organic components comprising contacting the mixture with an aqueous solution comprising an acid to convert at least a portion of the oxazole into an oxazole acid salt and to dissolve at least a portion the oxazole acid salt into the aqueous solution; separating the aqueous solution from the mixture; contacting the aqueous solution after separation from the mixture with a base to neutralize at least a portion of the oxazole acid salt to form released oxazole; and recovering at least a portion of the released oxazole. Prior to the neutralization step the aqueous solution separated from the mixture may be contacted with one or more organic solvents that are immiscible with the aqueous solution to extract organic components from the aqueous solution and reduce the level of organic components in the aqueous solution.

This invention is also process for the recovery of oxazole from a mixture comprising oxazole and one or more other organic components such as acetonitrile comprising reacting the mixture with an acid to convert at least a portion of the oxazole into a solid acid salt; separating the solid acid salt from the resulting mixture to form an isolated acid salt; contacting the isolated solid with a base to neutralize at least a portion of the solid acid salt and form released oxazole; and recovering at least a portion of the released oxazole. Prior to the step of reacting the solid acid salt of the oxazole with a base, the acid salt of the oxazole can be washed with one or more organic solvents to reduce the level of organic components in the acid salt of the oxazole.

DETAILED DESCRIPTION OF THE INVENTION

This invention is a process for the recovery of oxazole from mixtures comprising oxazole. The mixtures preferably contain oxazole and one or more other organic components. The mixture may also contain one or more inorganic components such as water or hydrogen cyanide (HCN). The amount of oxazole in the mixture comprising oxazole may be any amount but generally is no more than about 60 weight percent, for example about 10 to about 50 weight percent of the mixture. In the preferred process of this invention, the mixture comprising oxazole also comprises one or more of acrylonitrile, acetonitrile and water. Such mixtures can be obtained as process streams formed during the production of acrylonitrile by the catalytic ammoxidation of a feed such as propylene or propane. Preferably the mixture comprising oxazole comprises oxazole and acetonitrile preferably where the mixture is about 20 to about 80 weight percent acetonitrile, and more preferably about 30 to about 70 weight percent acetonitrile and about 1 to about 60 weight percent, more preferably about 1 to about 50 weight percent, and typically about 10 to about 40 weight percent oxazole.

Methods for the catalytic ammoxidation of such feeds are well known in the art. In such methods, a feed such as propylene or propane is reacted in the presence of a catalyst with ammonia and an oxygen-containing gas. The oxygen-containing gas may, for example, be air, air enriched with pure oxygen gas, or some other form of molecular oxygen. The catalyst is suitably one of a number of catalysts known in the art for the ammoxidation of a hydrocarbon such as propylene or propane. Suitable catalysts are disclosed for example in U.S. Pat. Nos. 3,642,930; 4,485,079; 3,911,089; 4,873,215; 4,877,764; and Japanese Patent Application Nos. 74-87474 and 78-352322 all of which are incorporated herein by reference in their entirety. In such ammoxidation processes acrylonitrile is produced as the major product. However, smaller amounts of other products such as HCN, acetonitrile, oxazole, allyl alcohol, acetone, and propionitrile are co-produced. Water is also formed. A condensed organic product mixture from the catalytic ammoxidation of a feed such as propylene may, for example, contain about 10 to about 13 weight percent acrylonitrile, about 16 to about 19 weight percent water, about 0.9 to about 1.5 weight percent HCN, about 0.2 to about 0.4 weight percent acetonitrile and about 1.0 to about 2.0 weight percent other organic compounds including oxazole, allyl alcohol, acetone and propionitrile. Suitable processes for the catalytic ammoxidation of propylene to acrylonitrile are disclosed in U.S. Pat. Nos. 5,093,299; 4,863,891; 4,767,878; and 4,503,001, all of which are hereby incorporated herein by reference in their entirety. After the ammoxidation reaction it is necessary to isolate the desired acrylonitrile. Co-products such as acetonitrile and HCN are also typically recovered from the reactor effluent. Process for the purification of acrylonitrile are, for example, set forth in U.S. Pat. Nos. 4,234,501; 3,885,928; 3,352,764; 3,198,750; and 3,044,966, which are hereby incorporated herein by reference in their entirety.

In a typical process for the isolation of acrylonitrile, the effluent from an ammoxidation reactor is treated to remove residual ammonia. The remaining mixture is suitably treated by a number of distillation processes to isolate the desired acrylonitrile. During this purification process, a product stream rich in acetonitrile is typically produced. Such an acetonitrile rich stream may contain about 30 to about 78 weight percent acetonitrile, about 20 to about 68 weight percent water, about 0.01 to about 10 weight percent HCN and about 1.0 to about 5.0 weight percent of other organics such as, for example, oxazole, allyl alcohol, acetone, and acrylonitrile. This stream can be distilled during the process to isolate acetonitrile, a valuable co-product. A process for the recovery of acetonitrile from such process streams is disclosed in U.S. Pat. No. 4,362,603 which is incorporated herein by reference in its entirety. In a first distillation column, this stream containing acetonitrile is distilled to produce an overhead, light-end stream, a middle fraction containing water and acetonitrile, and a bottom fraction. The overhead light-end stream may comprise up to about 40 to about 60 weight percent oxazole, typically about 10 to about 40 weight percent, about 10 to about 40 weight percent water, about 45 to about 60 weight percent acetonitrile and generally no more than about 15 weight percent other organic components such as acrylonitrile, acetone and methanol. The mixture also generally contains HCN, generally no more that about 2 or about 3 weight percent. Such a stream which can be produced during the purification of acetonitrile is one of the preferred process streams that can be used in the process of this invention to recover oxazole. While this is a useful process stream, it is not the only process stream that can be produced during the manufacture of acrylonitrile that may contain oxazole. Another preferred stream is the process stream produced as an overhead in the product column during the purification of acetonitrile by the process disclosed in U.S. Pat. No. 4,362,603, which is incorporated herein by reference in its entirety. Such a process stream contains oxazole and acetonitrile but generally contains low quantities of HCN. For example, such a process stream may comprise about 1 to about 60 weight percent oxazole, typically about 10 to about 40 weight percent, about 1 to about 20 weight percent water, about 45 to about 60 weight percent acetonitrile, about 0 to about 5 weight percent methanol, about 0 to about 15 weight percent acetone, about 0 to about 5 weight percent allyl alcohol and generally no more than about 300 ppm by weight, preferably no more than about 200 ppm by weight HCN. The remainder of the mixture is acetonitrile, generally about 40 to about 60 weight percent. Such a mixture is suitable for use in the process of this invention to recover oxazole. For example, using the process and apparatus disclosed in U.S. Pat. No. 4,362,603, a mixture comprising oxazole containing less than about 5000 ppm (by weight), more preferably less than about 1000 ppm, and most preferably less than about 100 ppm HCN can be produced. Such streams can also have less than about 500 ppm, preferably sell than about 50 ppm and most preferably less than about 10 ppm by weight acrylonitrile. Such streams can be prepared as an overhead from the product column using, for example, the process and apparatus disclosed in U.S. Pat. No. 4,362,603. In such process, the overhead from the product column, preferably a condensed portion in the form of a liquid stream, is recycled to the drying column and the heads column so that at least about 75 weight percent, and more preferably at least about 80 weight percent and most preferably at least about 85 weight percent of the overhead is recycled to the drying column. Such a process produces a product column overhead having desirably high levels of oxazole, such as the levels of oxazole in the mixtures comprising ozaxole mentioned above, and the desirably low levels of HCN and acrylonitrile as mentioned above. In one embodiment of the process of this invention, the oxazole present in a mixture is recovered from such mixture, such as the above described mixtures and particularly the above described mixtures isolated during the purification of acetonitrile, by converting at least portion of the oxazole into a water soluble acid salt and extracting at least a portion of the water soluble salt into an aqueous solution and then neutralizing at least a portion of the water soluble acid salt with a suitable base to release oxazole. In one such process, the mixture comprising the oxazole and also typically containing at least one other organic compound such as acetonitrile, is contacted with an aqueous acid solution, such as a solution of one or more strong acids, such as one or more of sulfuric acid, hydrochloric acid, hydrobromic acid, phosphoric acid and the like. Any acid is suitable provided it is a strong enough acid to protonate at least some and preferably all of the oxazole present and form an acid salt of the oxazole that is at least partially soluble in water. Sulfuric acid and hydrochloric acid are preferred acids for this purpose. Sulfuric acid is most preferred. When sulfuric acid is used to form the acid salt of oxazole, an oxazole sulfate is formed, such as oxazolium hydrogen sulfate. Preferably the acid has a pKa of less than about 1. More preferably the pKa is less than 1. The amount of acid present in the aqueous solution is preferably enough to react with and convert most and most preferably all of the oxazole present in the mixture to the acid salt. Preferably, the amount of water used to form the aqueous acid solution is such that the acid concentration is no more than about 70 weight percent acid. However, the amount of water used, and the amount and type of acid used to form the aqueous acid solution, is preferably selected so that when the aqueous acid solution is contacted with the mixture comprising the oxazole all or substantially all of the oxazole present in the mixture is converted to the acid salt and all or substantially all of the acid salt becomes dissolved in the resulting aqueous layer. By substantially all we mean, preferably, at least about 90 percent, more preferably at least about 95 percent and most preferably at least about 99 weight percent. While it may be advantageous to add water to the mixture to form the aqueous solution as describe above, there may be sufficient water in the mixture comprising oxazole so that it is not necessary to add additional water. In such cases, adding and acid to the mixture, such as concentrated sulfuric acid, will form the aqueous acid solution.

The contacting of the aqueous acid solution with the mixture comprising oxazole can take place in any convenient manner. Preferably, such contacting is conducted in a manner such that there is intimate contact between the aqueous acid solution and the mixture containing oxazole. For example, the aqueous acid solution and the mixture containing oxazole can be shaken together, rapidly stirred or otherwise agitated to result in intimate contact of the two phases, so that the oxazole can be converted to the acid salt and the acid salt formed can pass or transfer into the aqueous phase. The temperature during such contacting is any suitable temperature such as ambient temperature. If an exothermic reaction occurs, the mixture of aqueous acid and the mixture containing the oxazole can be cooled to maintain the ambient temperature. Since oxazole boils at around 70° C., it is advantageous to maintain the temperature during such contacting below that temperature.

It is to be understood that while it is preferable to extract all or substantially of the oxazole as its acid salt into the aqueous acid solution by contacting it with a single portion of aqueous acid solution, it is not necessary to do so. The contacting can comprise multiple steps of contacting an aqueous acid solution with the mixture comprising oxazole. Also, the process step of contacting an aqueous acid solution with the mixture comprising oxazole can be accomplished in a continuous manner using one or more apparatus available commercially to effect such extractions.

After the aqueous acid solution is contacted with the mixture containing the oxazole to convert the oxazole into its acid salt and to transfer at least a portion and preferably substantially all of the acid salt to the aqueous phase, the resulting aqueous phase is separated from the organic phase. Such separation can occur by any suitable means. One convenient means is to permit the mixture to settle so the aqueous phase, due to its immiscibility, separates from any organic phase if present. Generally, if the mixture containing oxazole used in the process has another organic component such as acetonitrile, the acetonitrile will form such separate organic phase. After separation of the phases, the phases can be conveniently separated by using, for example, a separation funnel or a decanter.

The next step in the process is to neutralize the oxazole acid salt to release the desired oxazole. However, prior to such neutralization process step, it is preferable to extract the aqueous solution containing the oxazole salt with one or more solvents and one or more times with each solvent. Extracting the aqueous solution containing the oxazole salt with a suitable solvent can be used to reduce the organic components in the aqueous solution. The amount of solvent used and the number of extractions, for example one to about three, will depend on the level of undesired organic components that are in the aqueous solution and will also depend on the purity of the oxazole desired. For example, the amount of solvent used for each extraction can be about 10 percent by volume to about 200 percent by volume of the aqueous solution. The solvent used is preferably a solvent that is immiscible with the aqueous phase. Solvents such as dichloromethane, chloroform, ether such as diethyl ether, a hydrocarbon such as toluene or other aromatic solvent, a mixture of pentanes or a mixture of hexanes are suitable. The chlorinated solvents such as chloroform or dichloromethane are preferred. The extraction is generally conducted at about ambient temperature using any suitable vessel or process equipment, although higher or lower temperatures can be used for such extraction. Commercially available extraction equipment can also be used for this part of the process. As described above for the contacting of the aqueous acid solution with the mixture comprising oxazole, it is desirable to conduct the extraction where there is intimate contact between the aqueous solution containing the acid salt of oxazole and the solvent used for the extraction. Such intimate contact can be achieved by shaking, stirring rapidly or otherwise agitating the mixture of the solvent and the aqueous phase containing the salt of the oxazole. In one simple method, after the solvent used for the extraction is agitated with the aqueous solution containing the salt of oxazole, the resulting mixture is permitted to settle so that the organic phase separates from the aqueous phase and the phases can be thereafter easily separated. The extraction can also be can be conducted in a continuous manner using, for example, commercially available extraction equipment.

After such extraction, or if no extraction is used, the aqueous solution containing the acid salt of the oxazole is treated to release oxazole. The treatment is suitably a neutralization reaction. Such neutralization is conveniently accomplished by contacting or mixing the aqueous solution containing the oxazole salt with a suitable base. Any suitable base can be used such as sodium hydroxide, potassium hydroxide, or other hydroxide of an alkali or alkaline earth metal, ammonium hydroxide and the like. The amount of base used is preferably an amount that will release all or substantially all of the oxazole from the salt to form free oxazole. By substantially we mean, preferably, at least about 95 weight percent, more preferably at least about 98 weight percent and most preferably at least about 99 weight percent. Any suitable means can be used to contact the base with the aqueous solution of the acid salt of oxazole. The base can be added as a solid or as a neat liquid to the aqueous solution. It can be added by bubbling or otherwise adding a base as a gas to the aqueous solution. The aqueous solution containing the solid acid salt of oxazole can be added to the base. It is preferred to agitate the mixture of the base and the aqueous solution of the oxazole acid salt to more efficiently effect the neutralization of the oxazole acid salt to free the desired oxazole. If the reaction becomes exothermic, it is preferred to cool the mixture during the neutralization step, preferably to a temperature below the boiling point of oxazole, more preferably below about 60 C., to prevent the oxazole from reaching its boiling point and otherwise reduce any losses of oxazole due to evaporation.

In a preferred embodiment of this invention, the neutralization step to convert the oxazole acid salt into oxazole is accomplished by contacting the aqueous solution of the oxazole acid salt with a slurry of a strong base such as potassium or sodium hydroxide or other alkali or alkaline earth hydroxide in water, preferably by adding the aqueous solution of the acid salt of the oxazole to the slurry. The slurry preferably contains sodium hydroxide or other strong base in amounts sufficient to neutralize any acid present in the aqueous mixture used to form the acid salt of oxazole as well as any other acid, such as HCN, that may be present, to absorb water, if any, in the process stream containing the oxazole as well as any water produced by the neutralization of the acid salt of the oxazole, and have up to at least about 10 molar percent excess of base over the molar amount of oxazole acid salt being neutralized. Using sodium hydroxide as an example, the amount of water used to form the slurry is preferably such that the weight ratio of sodium hydroxide to water is about 3:1 to about 1.5:1, most preferably about 2:1. Preferably such neutralization is conducted at a low temperature preferably by maintaining the slurry at a low temperature. The temperature, for example, below the boiling point of oxazole, should preferably be about 30° C. or below, more preferably about 20° C. to about 10 C.

After the acid salt of the oxazole is reacted with base to release oxazole, the oxazole released is separated from the mixture by one or more suitable means such as by decanting the liquid, distilling the oxazole directly from the mixture or any other suitable means for separating the oxazole from the mixture after neutralization. After the oxazole is separated it can be further treated by drying with one or more suitable drying agents such as sodium or potassium hydroxide or molecular sieves to reduce the level of water present. For example, the separated oxazole can be contacted with an amount sodium hydroxide in pellet, powder or other solid granular form to reduce the amount of water present in the oxazole to a desired level. The oxazole can after such drying treatment be further purified by, for example, distillation at atmospheric or at reduced or elevated pressure. Oxazole produced in such a manner can have a purity of at least about 98 weight percent, more preferably at least about 99 weight percent.

Each of the process steps described hereinabove can be practiced in a batch-type manner, or one or more or all of the steps can be practiced in a continuous manner.

In another embodiment of the process of this invention, the oxazole acid salt is isolated as a solid before it is treated to form oxazole. The solid oxazole acid salt such as, for example, an oxazole sulfate may, prior to a treatment such as neutralization, be washed, dried or otherwise treated to reduce or eliminate any unwanted components or impurities.

In this embodiment of the invention, mixtures comprising oxazole, such as the mixtures described hereinabove comprising oxazole, are treated with an acid, preferably a strong acid, for example, one or more of the acids described hereinabove, to convert the oxazole into the oxazole acid salt, the oxazole acid salt is separated from the mixture, preferably washed with a suitable solvent to remove residual organic components, preferably dried to reduce or eliminate any residual solvent, and then converted to oxazole preferably by reacting the oxazole acid salt with a suitable base to release the desired oxazole. The oxazole released can be separated from the resulting mixture by one or more suitable methods such as by decantation or distillation. The oxazole separated can be further purified.

In more detail, in this embodiment of the invention, oxazole is isolated from a mixture comprising oxazole, preferably a mixture comprising acetonitrile and more preferably the mixtures comprising oxazole and acetonitrile as described above, and most preferably the process streams comprising oxazole and acetonitrile isolated during the purification of acetonitrile as those described hereinabove. Most preferably, the mixture used is the mixture comprising oxazole and acetonitrile and comprising low levels of HCN, such as less than about 300 parts by million by weigh HCN, for example, the process streams comprising oxazole described herein above isolated during the purification of acetonitrile.

The mixture comprising oxazole is treated with an acid, preferably one or more of the strong acids described hereinabove, to convert at least some and preferably all of the oxazole present in the mixture to its acid salt. The acid can be one or more strong acids, such as one or more of sulfuric acid, hydrochloric acid, hydrobromic acid, phosphoric acid and the like. Any acid is suitable provided it is a strong enough acid to protonate at least some and preferably all of the oxazole present and form an acid salt of the oxazole. Sulfuric acid and hydrochloric acid are preferred acids for this purpose. Sulfuric acid is most preferred. Preferably the acid has a pKa of less than about 1. More preferably the pKa is less than 1. The amount of acid used is preferably enough to convert most and most preferable substantially all of the oxazole present in the mixture to the solid acid salt. An acidic resin, for example an acidic ion exchange resin, can be used as the acid. By substantially all we mean, preferably, at least about 90 weight percent, more preferably at least about 95 weight percent and most preferably at least about 99 weight percent. Preferably at least a stoichiometrically equivalent amount of acid is used to convert the oxazole to the oxazole acid salt, i.e., at least about one mole of acid per mole of oxazole present in the mixture. The treatment or reaction with acid may be exothermic. The reaction, if exothermic, should be cooled in order to maintain the temperature below the boiling point of oxazole. Preferably, the temperature of the mixture during the reaction with the acid is maintained at no more than about 50° C., more preferably at a temperature of no more than about 40° C. The mixture comprising oxazole can be added to the acid or, more preferably, the acid can be added to the mixture comprising oxazole. It is preferred to mix the acid with the mixture comprising oxazole slowly so that the reaction to form the oxazole acid salt can be controlled.

Preferably, prior to treating the mixture comprising oxazole with acid to form the oxazole acid salt, or at any time it is desirable to purify oxazole or a mixture comprising oxazole, the oxazole or a mixture, such as the mixtures described hereinabove comprising oxazole, is treated with at least one base such as sodium hydroxide, potassium hydroxide or a some other hydroxides of the other alkali or alkaline earth metals. Preferably the base is a strong base and more preferably it is sodium or potassium hydroxide, most preferably it is sodium hydroxide. The amount of strong base used is preferably an amount to remove all or substantially all of the water, if present, from the mixture comprising oxazole and, if present, all or substantially all of the HCN. By substantially all we mean, preferably, at least about 95 weight percent, more preferably at least about 98 weight percent and most preferably at least about 99 weight percent. Preferably, the base such as sodium hydroxide or potassium hydroxide, is used in pellet, granular or powder form. For example, commercially available sodium hydroxide pellets can be used. The amount of base used can be, for example, about 2 to about 4 moles of base for each mole of water present in the mixture and about 1 to about 2 moles of base for each mole of HCN, if present in the mixture. When the mixture comprises oxazole, acetonitrile and water, the addition of a strong base such as sodium hydroxide typically results in a two phase mixture where oxazole and acetonitrile are present in the upper organic phase of the two phase mixture, and water and sodium hydroxide are present in the lower phase. The separation of the upper phase from the lower phase provides for a mixture comprising oxazole containing low levels of water and HCN, for example, no more than about 3 weight percent water, preferably no more than about 2 weight percent water, and preferably no more than about 200 ppm, by weight, HCN, more preferably no more than about 100 ppm HCN. The upper phase containing oxazole, preferably after separation from the base, can optionally be distilled either at atmospheric or reduced pressure. During the step of contacting the mixture comprising oxazole with a strong base it is preferred to maintain the mixture below the boiling temperature of oxazole, for example, at a temperature of no more than about 30° C., preferably about 10 to about 30° C., most preferably about 10 to about 20° C. It is preferable to maintain the strong base in contact with the mixture comprising oxazole for more than an hour, for example for about 1 to about 20 hours, more preferably for about 10 to about 20 hours.

In order to assist in subsequent separation steps of the solid oxazole acid salt after reaction with acid, and also to assist with handling, for example stirring or transferring the oxazole acid salt from one vessel or apparatus to another, it is preferable to include a quantity of solvent along with the oxazole acid salt. The solvent can be added prior to, during or subsequent to the step where the acid is reacted with the mixture to form the solid acid salt of oxazole. The solvent can be any suitable solvent but preferably one that does not appreciably dissolve the oxazole acid salt. Preferably the solvent is one or more organic solvents such as dichloromethane, chloroform, an ether, such as diethyl ether, a hydrocarbon such as toluene or other aromatic hydrocarbon, a mixture of pentanes or a mixture of hexanes, and acetonitrile. Acetonitrile is the preferred solvent for this purpose. The amount of solvent, if used, is preferably an amount such that the solid oxazole salt is not more than about 30 weight percent of the resulting mixture of oxazole acid salt and solvent.

After reaction to form the acid salt of oxazole, the acid salt is separated from the remaining components. The separation can be accomplished by any suitable means such as by atmospheric or vacuum assisted filtration, centrifugation and the like. Filtration is preferred. The solid oxazole acid salt separated can be washed with one or more solvents such as the solvents described hereinabove by, for example, contacting the oxazole acid salt with the solvent followed by separating the solvent from the oxazole acid salt by, for example, filtration, such as vacuum assisted filtration, or centrifugation, and then drying the oxazole acid salt to remove any residual solvent. If the oxazole acid salt is washed with a solvent, it is generally preferable to conduct the washing at a low temperature, such as at a temperature below the boiling point of oxazole, for example, at a temperature of no more than about 30° C., more preferably no more than about 20° C. The washing assists with the removal of any unwanted organic components from the oxazole acid salt. The solvent for washing can be any suitable solvent but preferably one that does not appreciably dissolve the oxazole acid salt. Preferably the solvent for washing is one or more organic solvents such as dichloromethane, chloroform, an ether, such as diethyl ether, a hydrocarbon such as toluene or other aromatic hydrocarbon, a mixture of pentanes or a mixture of hexanes, and acetonitrile. Acetonitrile is the preferred solvent for this purpose. Drying is conveniently accomplished by heating the oxazole acid salt at an elevated temperature and preferably at reduced pressure. For example, a temperature of no more than about 60° C. The pressure can be atmospheric or preferably a reduced pressure, for example a pressure of about 25 mmHg or below. The drying can be conducted for about 1 to about 2 hours.

After separation and optional washing and drying, the solid acid oxazole salt is treated to form the desired oxazole. Preferably, it is neutralized with a base to release the desired oxazole. Any suitable base can be used such as sodium hydroxide, potassium hydroxide or other hydroxide of an alkali or alkaline earth metal, ammonium hydroxide and the like. Preferably the base is potassium or sodium hydroxide. Most preferably it is sodium hydroxide. The amount of base used is preferably an amount that will release all or substantially all of the oxazole from the salt to form the free oxazole. By substantially we mean, preferably, at least about 95 weight percent, more preferably at least about 98 weight percent, and most preferably at least about 99 weight percent. In this neutralization step, the solid oxazole acid salt, either as a neat solid or as a solution in water, can be added to the base, preferably where the base is dissolved in water. Alternatively, a base or a solution of a base can be added to the solid oxazole acid salt, preferably as an aqueous solution of the acid salt of oxazole.

If the oxazole acid salt is added as an aqueous solution to the base, the amount of water used is preferably kept to a minimum. For example, in such embodiment, the base, such as sodium hydroxide, preferably in an amount required to neutralize the acid salt of oxazole salt, for example, at least a stoichiometrically equivalent amount, is dissolved in a minimum amount of water required to dissolve the base. The acid salt of the oxazole is dissolved in a minimum amount of water. Preferably, the amount of water used for both the dissolution of the base and the acid salt of the oxazole should be no more than about 10 moles of water per mole of the acid salt of oxazole. If too much water is used it is possible that after the neutralization reaction to convert the acid salt of oxazole to free oxazole, a separation of the aqueous phase from the phase containing oxazole will not occur. However, it is desirable for such a separation to occur so that the oxazole can be separated from the aqueous phase containing the base. The amount of water used to dissolve the acid salt of oxazole combined with the amount of water used to dissolve the base such as sodium hydroxide should be an amount that provides for a separation of the resulting mixture into two phases, an aqueous phase containing the base and the salt formed during the neutralization of the acid salt of oxazole (for example sodium sulfate when sodium hydroxide is used to convert the sulfuric acid salt of oxazole to oxazole) as well as any other water soluble components, and an organic phase containing oxazole. As mentioned above, it is not necessary to add the acid salt of oxazole to the base as an aqueous solution; however, it is preferable to do so rather than adding solid oxazole to the aqueous base.

Alternatively, and preferably, the base, preferably an aqueous solution of the base, in the amounts described above can be added to an aqueous solution of the acid salt of oxazole to convert the acid salt of oxazole to free oxazole. As described above, it is preferable to use a minimum amount of water necessary so that after the reaction to convert the acid salt of oxazole to free oxazole, there is a phase separation as described above. Preferably, the amount of water used for both the dissolution of the base and the acid salt of the oxazole should be no more than about 10 moles of water per mole of the acid salt of oxazole.

During the reaction to convert the acid salt of oxazole to free oxazole, the temperature of the temperature should be maintained below the boiling point of oxazole. Preferably, the temperature should be maintained at no more than about 50° C.

After the reaction of the acid salt of oxazole with a base to form free oxazole, the free oxazole is separated from the resulting mixture. The separation can be accomplished by any suitable means such as decantation or distillation. For example, the free oxazole can be distilled directly from the mixture either at atmospheric pressure or at a pressure above or below atmospheric pressure. If, as described above, there is a separate phase containing oxazole and a phase containing water and the salt formed by the reaction of base with the acid salt of oxazole, such phase containing oxazole can be separated from the phase containing water by, for example, decantation or using a separatory funnel. The phase containing oxazole can be distilled or purified further by other purification methods. Prior to such distillation or other purification, the oxazole can be treated with a base such as sodium hydroxide, potassium hydroxide or other hydroxide of an alkaline or alkaline earth metal base to remove water, if present. The amount of base added should be an amount that will remove all or substantially all of the water if present in the oxazole. Preferably the base is in the form of a pellet or other granular, powder or other particulate form. Commercially available sodium or potassium hydroxide pellets are preferred for this purpose. By substantially we mean, preferably, that the resulting oxazole contains no more than about 2 weight percent water, more preferably no more than about 1 weight percent water. The oxazole treated with base in this manner can be distilled at atmospheric pressure or at a pressure above or below atmospheric pressure. The distillate can be treated with a base such as sodium or potassium hydroxide or other hydroxide of an alkaline or alkaline earth metal to remove or reduce the amount of any water that may be present in the oxazole. The oxazole can also be treated with other agents to remove water such as molecular sieves. Oxazole produced in this manner can have a purity of at least about 98 weight percent, more preferably at least about 99 weight percent.

The following examples describe certain embodiments of the above-described invention but are not to be construed as limiting in any way the scope thereof.

EXAMPLES

Example 1

To a 100 gr. (gram) sample of a mixture composed of 11 weight percent oxazole, 1.67 weight percent HCN, 16 weight percent water, 12 weight percent acrylonitrile, 1 weight percent methanol, and the balance acetonitrile in a 250 ml round bottom flask was added dropwise 33.66 gr. (0.34 moles) of concentrated sulfuric acid. Two layers formed. The aqueous layer, which contained>99% of the oxazole as oxazolium hydrogen sulfate, was decanted from the organic layer. The aqueous layer was then extracted three times with 35 ml (milliliter) portions of dichloromethane in a 125 ml separatory funnel.

After the extraction, the aqueous layer was added dropwise to a mechanically stirred slurry of 32 gr. (0.8 moles) of NaOH in 21 gr. water cooled to 10° C. Two layers formed; the upper layer was mostly oxazole, and the lower layer contained aqueous and solid sodium sulfate decahydrate. The mixture was distilled directly. Crude oxazole, 9.94 gr., was collected as the fraction distilling between 68°–71° C. This distillate, which contained 6 weight percent water, was then stirred with 1.0 gr. of NaOH for one hour and then redistilled. The fraction boiling from 69°–70° C., 7.0 gr. (98.4 weight percent oxazole, 1.06 weight percent acetonitrile, 0.2 weight percent methanol, 0.24 weight percent dichloromethane, and 0.11 weight percent water) was collected. The overall yield of oxazole was 63%.

Example 2

50 gr. of a mixture as described in Example 1 was charged into a 100 ml, three neck, round bottom flask. The flask was equipped with a cold-finger condenser, gas dispersion tube, glass stopper, and magnetic stirring bar. A drying tube charged with a solid desiccant was connected to the condenser; the drying tube served as a vent. The condenser was cooled to −78° C. with a mixture of dry ice and acetone. The gas dispersion tube was connected to a lecture bottle of HCl gas with a length of polyvinyl chloride tubing. The flow of HCl gas from the lecture bottle was adjusted with a manual control valve. The flask was immersed into an ice bath. After the mixture cooled to 0° C., 5.33 gr. of HCl gas (0.146 moles) was bubbled into it. The mixture immediately separated into two layers.

The aqueous layer was separated from the organic layer then extracted three times with 15 ml portions of dichloromethane in a 60 ml separatory funnel. After the extraction, the aqueous layer was added dropwise to a mechanically stirred slurry of 17 gr. of NaOH (0.425 moles) in 8 gr. of water cooled to 10° C. Two layers formed; the upper layer was mostly oxazole, and the lower layer contained aqueous and solid sodium chloride. The mixture was distilled directly. Crude oxazole, 4.60 gr., was collected as the fraction distilling between 68°–71° C. This distillate, which contained 6 weight percent water, was then stirred with 1.0 gr. of NaOH for one hour and then redistilled. The fraction boiling from 69°–70° C., 3.8 gr. (98.4weight percent oxazole, 1.06 weight percent acetonitrile, 0.2 weight percent methanol, 0.24 weight percent dichloromethane, and 0.11 weight percent water) was collected. The overall yield of oxazole was 67%.

Example 3

A mixture (112 gr.) containing 32 weight percent oxazole, 2.86 weight percent HCN, 15 weight percent water and the balance acetonitrile was stirred with 20 gr. sodium hydroxide pellets for one hour at room temperature in a 250 ml three neck flask with a mechanical stirrer and two rubber septa. Two layers formed. HCN was converted to NaCN and extracted into the lower aqueous layer, and the upper organic layer contained less than 1 weight percent water. The organic layer was decanted from the aqueous layer and distilled at ambient pressure. Most of the organic layer distilled between 60° C. and 92° C. and had the composition of 43 weight percent oxazole and the balance acetonitrile. Concentrated sulfuric acid (51.5 gr.) was added dropwise to the distillate with efficient stirring in a three neck flask fitted with a mechanical stirrer, addition funnel, and a filter stick through a septum. The temperature of the contents of the flask was maintained at between 5° C. and 20° C. during the addition using an ice bath. Oxazole sulfate precipitated immediately as it was formed. After acid addition was complete, the supernatant acetonitrile was removed by aspiration through the filter stick while dry air was added through the flask. The oxazole sulfate was washed with five portions of diethyl ether and each portion of the ether was removed by aspiration through the filterstick. Residual ether was removed on a rotary evaporator. The yield of oxazole sulfate was 96%.

The dried, pure white oxazole sulfate was added in small portions to a vigorously stirred solution of 40.8 gr. of sodium hydroxide in 73.4 gr. of water in a three neck flask fitted with a mechanical stirrer while the temperature was maintained below 20° C. Stirring was stopped after the addition of oxazole sulfate was complete. Two layers formed. The upper layer was nearly pure oxazole and the lower layer contained nearly pure sodium sulfate decahydrate. The mixture was distilled directly. Oxazole was collected as the fraction distilling between 68 and 71° C. This distillate, which contained 8.8 weight percent water was stirred with 6.9 gr. of sodium hydroxide for one hour and redistilled. The fraction boiling from 69° C. to 70° C. was collected as oxazole and weighed 32 gr. for a yield of 89%.

Example 4

A mixture (2431 gr.) containing 34.4 weight percent oxazole, 19.0 weight percent water, 2.8 weight percent methanol, 0.4 weight percent acetone, 0.0015 weight percent HCN and 43.4 weight percent acetonitrile was stirred with 411 gr. (10.3 mole) NaOH for 1 hour at room temperature in a 5 liter three-neck flask fitted with a mechanical stirrer and thermometer. Two layers formed and the organic phase (Sample A, 1891 g) was separated by decantation and analyzed (Table I). Yield of contained oxazole on this step was 96%.

TABLE I

Sample A Composition

| Component | Wt. % |
|---|---|
| Methanol | 2.4 |
| Acetone | 0.5 |
| Acetonitrile | 53.4 |
| Water | 1.3 |
| Oxazole | 42.4 |

The organic layer (1891 gr., containing 42.4 weight percent oxazole (802 gr., 11.6 mole) was placed in a 5-liter three-neck flask fitted with a mechanical stirrer, thermometer and an addition funnel containing concentrated sulfuric acid (96.7%). The solution was cooled to 10° C. using an external ice bath and the sulfuric acid (641 ml, 1179 gr. 11.6 mole) was added dropwise maintaining the temperature of the reaction mixture below 40° C. (Total addition time was about 3 hours). A white solid (oxazole sulfate) precipitated immediately upon addition of the sulfuric acid and the mixture became quite viscous toward the later part of the reaction. The suspension was cooled to 10° C. using an external ice bath (to reduce the solubility of oxazole sulfate in acetonitrile) and the supernatant organic components removed using a filter stick in inserted through a rubber septum. The resulting white solid was washed twice with diethyl ether (2×500 ml) and the ether removed using the filter stick. The solid was transferred to four 1-liter flasks and dried using rotary evaporator at 60° C. under full vacuum for 1.5 hours. Total yield of dried oxazole sulfate was 1891 gr (97%).

Sodium hydroxide (426 gr. 10.6 mole) was dissolved in 350 gr. (19.4 mole) water in a 3-liter, three-neck flask fitted with a mechanical stirrer, thermometer and addition funnel. The solution was cooled to 10° C using an external ice bath and a solution of oxazole sulfate (886.4 gr., 5.31 mole) in water (440 gr., 24.4 mole) was added dropwise, maintaining the temperature below 50° C. A white solid ($Na_2SO_4$) precipitated immediately upon addition (Total addition time was about 1.5 hours.). Stirring was stopped and two layers formed in the flask (a colorless aqueous layer containing $Na_2SO_4$ and an amber organic layer containing oxazole). The mixture was distilled directly (68–90° C.) to afford the oxazole-water azeotrope as a colorless liquid (372 gr.) containing 91 weight percent oxazole (<0.1% organic impurities) and 9 weight percent water (92% yield based on contained oxazole).

Impure oxazole (372 gr., 4.9 mole, containing 9 weight percent water) was stirred with 30 gr. (0.75 mole) NaOH for 0.5 hour at room temperature. Two layers formed and the organic phase (334 gr.) was separated by decantation and isolated to afford oxazole containing 1.1 weight percent water (organic impurities<0.1 weight percent). Yield of oxazole from this step was 98%. Yield of oxazole starting from the original mixture was 84%.

U.S. Provisional Application 60/438,419 having a filing date of Jan. 7, 2003 is incorporated herein by reference and U.S. Provisional Application No. 60/442,359 having a filing date of Jan. 24, 2003, is also incorporated herein by reference.

Having described the invention, that which is claimed is:

1. A continuous process for the recovery of oxazole from a mixture comprising oxazole and acetonitrile comprising:
contacting the mixture with an aqueous solution comprising an acid to convert at least a portion of the oxazole into an oxazole acid salt and to dissolve at least a portion the oxazole acid salt into the aqueous solution;
separating the aqueous solution comprising the dissolved oxazole acid salt from the mixture;
contacting the aqueous solution after separation with a base to neutralize at least a portion of the oxazole acid salt to form released oxazole; and
recovering at least a portion of the released oxazole.

2. The process of claim 1 wherein the mixture comprises about 1 to about 60 weight percent oxazole and about 1 to about 80 weight percent acetonitrile.

3. The process of claim 1 wherein the mixture comprises about 10 to about 60 weight percent oxazole and about 10 to about 80 weight percent acetonitrile.

4. The process of claim 1 wherein the mixture comprising oxazole and acetonitrile comprises about 10 to about 40 weight percent oxazole, up to about 3 weight percent hydrogen cyanide, about 10 to about 40 weight percent water, and about 45 to about 60 weight percent acetonitrile.

5. The process of claim 1 wherein the mixture comprising oxazole and acetonitrile comprises about 10 to about 60 weight percent oxazole, about 1 to about 20 weight percent water, about 40 to about 60 weight percent acetonitrile, about 0 to about 5 weight percent methanol, about 0 to about 15 weight percent acetone, about 0 to about 5 weight percent allyl alcohol and no more than about 300 ppm by weight hydrogen cyanide.

6. The process of claim 1 wherein the acid comprises sulfuric acid.

7. The process of claim 1 wherein the base comprises sodium hydroxide.

8. A continuous process for the recovery of oxazole comprising:
contacting a mixture comprising oxazole and acetonitrile with an acid to form an acid salt of oxazole;
separating the acid salt of the oxazole from the mixture;
neutralizing the acid salt of oxazole separated from the mixture to release oxazole.

9. The process of claim 8 wherein the mixture comprises about 1 to about 60 weight percent oxazole and about 1 to about 80 weight percent acetonitrile.

10. The process of claim 8 wherein the mixture comprises about 10 to about 60 weight percent oxazole and about 10 to about 80 weight percent acetonitrile.

11. The process of claim 8 wherein the mixture comprises about 10 to about 40 weight percent oxazole, up to about 3 weight percent hydrogen cyanide, about 10 to about 40 weight percent water, and about 45 to about 60 weight percent acetonitrile.

12. The process of claim 8 wherein the mixture comprises about 10 to about 60 weight percent oxazole, about 1 to about 20 weight percent water, about 40 to about 60 weight percent acetonitrile, about 0 to about 5 weight percent methanol, about 0 to about 15 weight percent acetone, about 0 to about 5 weight percent allyl alcohol and no more than about 300 ppm by weight hydrogen cyanide.

13. The process of claim 8 wherein the acid comprises sulfuric acid.

14. The process of claim 8 wherein the neutralization comprises reacting the acid salt with a base.

15. The process of claim 14 wherein the base comprises sodium hydroxide.

16. The process of claim 8 wherein prior to contacting the mixture with an acid to form the acid salt of oxazole, the mixture is contacted with a base.

17. The process of claim 16 wherein the base is one or more of sodium hydroxide or potassium hydroxide.

18. The process of claim 16 wherein the mixture comprises water and the amount of base used is about 2 to about 4 moles of base per mole of water present.

* * * * *